United States Patent [19]

Giannessi et al.

[11] Patent Number: 5,102,896

[45] Date of Patent: Apr. 7, 1992

[54] 1-ACYL-2-PYRROLIDINONES AS ENHANCERS OF LEARNING AND MEMORY

[75] Inventors: Fabio Giannessi; Orlando Ghirardi; Domenico Misiti; Maria O. Tinti, all of Rome, Italy

[73] Assignee: Sigma-Tau Industrie Farmaceutiche Riunite S.p.A., Rome, Italy

[21] Appl. No.: 536,275

[22] Filed: Jun. 11, 1990

[30] Foreign Application Priority Data

Jun. 12, 1989 [IT] Italy ................... 48072 A/89

[51] Int. Cl.$^5$ ................ A61K 31/40; A61K 31/44; C07D 401/06; C07D 403/06
[52] U.S. Cl. .................... 514/343; 514/422; 514/423; 548/518; 548/539; 548/540
[58] Field of Search .......... 548/539, 540, 518; 514/343, 423, 422

[56] References Cited

PUBLICATIONS

C.A., 85:123730a, Ishida et al. (1976).
C.A., 88:169981y, Ishida et al. (1978).
C.A., 106:98125z, Maekawa et al. (1987).
C.A., 106:105417b, Maekawa et al. (1987).

Primary Examiner—Joseph Paul Brust
Attorney, Agent, or Firm—Oblon, Spivak, McClelland, Maier & Neustadt

[57] ABSTRACT 1-acyl-2-pyrrolidinones of general formula (I)

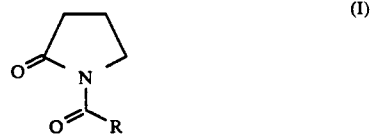

wherein R is selected from the group consisting of:
phenyl substituted with halogen-substituted lower ($C_1$–$C_4$) alkyl;
phenylalkyl wherein the alkyl moiety has 2–4 carbon atoms;
phenylalkenyl wherein the alkenyl moiety has 2–4 carbon atoms and the phenyl moiety is substituted with halogen-substituted lower ($C_1$–$C_4$)alkyl;
N-substituted pyrrolidin-2-yl; and
pyrid-3-yl are potent enhancers of learning and memory.
Orally or parenterally administrable pharmaceutical compositions in unit dosage form comprise from about 100 to 500 mg of one of the compound of formula (I).

2 Claims, No Drawings

1-ACYL-2-PYRROLIDINONES AS ENHANCERS OF LEARNING AND MEMORY

The present invention relates to 1-acyl-2-pyrrolidinones of general formula (I).

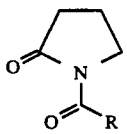

wherein R is selected from the group consisting of:
phenyl substituted with halogen-substituted lower ($C_1$-$C_4$) alkyl;
phenylalkyl wherein the alkyl moiety has 2-4 carbon atoms;
phenylalkenyl wherein the alkenyl moiety has 2-4 carbon atoms and the phenyl moiety is substituted with halogen-substituted lower ($C_1$-$C_4$)alkyl; and N-substituted pyrrolidin-2-yl.

The compounds of formula (I) are potent enhancers of learning and memory and are, therefore, useful nootropic agents.

The present invention also relates to orally or parenterally administrable pharmaceutical compositions for enhancing learning and memory, which comprise, as active ingredient, a compound of general formula (I) wherein R, in addition to the afore-said meanings, can also be pyrid-3-yl. The corresponding compound, 1-nicotinoyl-2-pyrrolidinone, is, unlike the other compounds, a known compound (cfr. J. Org. Chem. 37, 1635, 1972).

However, no pharmacological activity has ever been disclosed for this compound. The Japanese patent application (Tokkyo Koho) 8103026 discloses the utility of this compound as tobacco's flavouring agent.

The known compound that structurally and pharmacologically is the closest one to the compound of general formula (I) is aniracetam, 1-(p-methoxybenzoyl)-2-pyrrolidinone (cfr., e.g., Drugs of the future 6/3, 127, 1981 and the Canadian patent 1,100,515). As will be shown hereinbelow, the compounds of the present invention are more potent than aniracetam.

The compounds of the present invention are prepared via a process similar to that disclosed in the afore-said Canadian patent for preparing aniracetam. More particularly, the suitable aromatic or alkylaromatic or heterocyclic carboxylic acid is first converted to the acid chloride with halogenating agents, such as thionyl chloride or oxalyl chloride, at 25° C.-80° C., for 1-24 hours. The raw acid chloride is then condensed with 2-pyrrolidinone in inert solvents, such as methylene chloride, chloroform or ethyl ether in the presence of organic bases such as triethylamine, dimethylaminopyridine or pyridine, at 10° C.-30° C., for 8-48 hours.

The raw reaction product is purified by chromatography on a silica gel column using a gradient of ethyl acetate:hexane or chloroform as eluant, or by ion exchange chromatography with weak basic resins, such as AMBERLIST A21.

The following non-limiting examples illustrate the preparation of some compounds according to the invention.

EXAMPLE 1

Preparation of 1-(m-trifluoromethylbenzoyl)-2-pyrrolidinone (ST 628).

1st Step

Preparation of the acid chloride of m-trifluoromethyl benzoic acid.

Thionyl chloride (8.7 ml; 0.12 moles) was added to m-trifluoromethyl benzoic acid (11.4 g; 0.06 moles).

The solution was kept at 80° C. for 1 hour. It was then concentrated under vacuum and washed several times with ethyl ether. The raw reaction product was used as such in the succeeding step.

2nd Step

Preparation of 1-(m-trifluoromethylbenzoyl)-2-pyrrolidinone.

To a solution of m-trifluoromethylbenzoyl chloride (12.51 g; 0.06 moles) in 20 ml methylene chloride, a solution of 2-pyrrolidinone (6.8 g; 0.08 moles) and triethylamine (8.36 ml; 0.06 moles) in 20 ml methylene chloride, was slowly added under stirring.

The solution was kept at room temperature for 20 hours under stirring and then concentrated under vacuum.

The residue thus obtained was taken up with ethyl acetate. The precipitated triethylammonium chloride was filtered off and the organic phase was washed with 1N HCl, then with saturated solutions of $NaHCO_3$ and NaCl, and subsequently dried over anhydrous sodium sulphate and finally brought to dryness. 12.38 g of a raw product were obtained which was chromatographed on silica gel, using ethylacetate:hexane, ratio 1:1, as eluant. 5 g of the desired product were obtained.

Yield: 32%.

TLC: silica gel; eluant: ethylacetate:hexane, 1:1.
Rf: 0.6.

$^1$HNMR($CDCl_3$)δ7.8-7.2(m, 4H, aromatic);

4.0(t, 2H, $CH_2-N-\overset{O}{\underset{\|}{C}}$); 2.8-2.4(M, 2H, $CH_2-\underline{CH_2}-\overset{O}{\underset{\|}{C}}N-$);

2.4-1.8(m, 2H, $\underline{CH_2}-CH_2-\overset{O}{\underset{\|}{C}}N-$)

HPLC: μ Bondapack-C18 ∅: 3.9 mm L=300 mm size=10μ eluant; $KH_2PO_4$ 0.05M/$CH_3CN$ (65.35)
Flow rate: 1 ml/min
Retention Time: 30.62 min
Elementary analysis: ($C_{12}H_{10}F_3NO_2$); Calculated (%): C, 56.03; H, 3.90; N 5.4. Found (%): C, 55.50; H, 3.86; N, 5.15.

EXAMPLE 2

Preparation of 1-(m-trifluoromethylcinnamoyl)-2-pyrrolidinone (ST 623).

The product was prepared as described in example 1.
The acid chloride, pyrrolidinone and triethylamine were reacted at 1:1:1 ratio. Chromatography on silica gel was conducted with chloroform as eluant.
Yield: 28%
M.P.: 96°-98° C.

TLC: silica gel; eluant: chloroform
RF: 0.25
Elementary analysis; ($C_{14}H_{12}F_3NO_2$); Calculated (%): C, 59.36; H, 4.27; N, 4.94. Found (%): C, 59.62; H, 4.13; N, 4.9.

$^1$H NMR (CDCl$_3$) δ8.2–7.3 (m, 6H, aromatic; C$\underline{H}$=C$\underline{H}$); 3.9

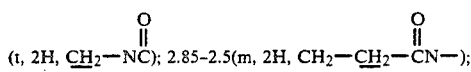
(t, 2H, C$\underline{H}_2$—NC); 2.85-2.5(m, 2H, CH$_2$—C$\underline{H}_2$—CN—);

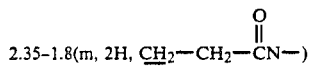
2.35-1.8(m, 2H, C$\underline{H}_2$—CH$_2$—CN—)

HPLC
TECHOPACK-C18: ⌀=4 mm, L=300 mm, size=10μ
Eluant: KH$_2$PO$_4$ 0.05M/CH$_3$CN (60/40)
Flow rate: 1.5 ml/min
Retention Time=18.46 min

EXAMPLE 3

Preparation of 1-(p-trifluoromethylbenzoyl)-2-pyrrolidinone (ST 643)

The product was prepared as described in example 1.
The acid chloride, pyrrolidinone and triethylamine were reacted at 1:2:1 ratio.
The final product was purified via ion exchange chromatography with the weak basic resin AMBERLIST A21 in methanol.
Yield: 18%
M.P.: 142°–143° C.
TLC silica gel; eluant: ethyl acetate:hexane 1:1
Rf: 0.4
Elementary analysis: ($C_{12}H_{10}F_3NO_2$); Calculated (%): C, 56.0; H, 3.91; N, 5.4. Found (%): C, 55.6; H, 3.9; N, 5.35.

$^1$H NMR (CDCl$_3$): δ7.75–7.2 (s, 4H, aromatic);

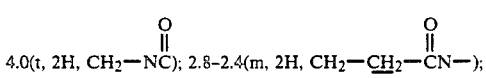
4.0(t, 2H, C$\underline{H}_2$—NC); 2.8-2.4(m, 2H, CH$_2$—C$\underline{H}_2$—CN—);

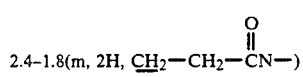
2.4-1.8(m, 2H, C$\underline{H}_2$—CH$_2$—CN—)

HPLC
μ Bondapack-NH$_2$: L=300 mm, ⌀=3.9 mm, size 10μ
eluant: KH$_2$PO$_4$ 0.05/CH$_3$CN (65/35)
Flow rate: 1 ml/min
pH: 5.2
isocratic
Retention Time=2.82 min

EXAMPLE 4

Preparation of 1-(4-phenylbutanoyl)-2-pyrrolidinone (ST 678)

The product was prepared as in example 1.
The acid chloride, pyrrolidinone and triethylamine were reacted at 1:3:1 ratio.
Chromatography on silica gel was conducted with ethyl acetate:hexane (ratio: 4:6) as eluant.
Yield: 52%
M.P.: 47°–48° C.
TLC: silica gel; eluant: ethyl acetate:hexane 1:1
RF: 0.68
Elementary analysis: ($C_{14}H_{17}NO_2$); Calculated (%): C, 72.70; H, 7.41; N, 6.05. Found (%): C, 72.39; H, 7.56; N, 5.95.

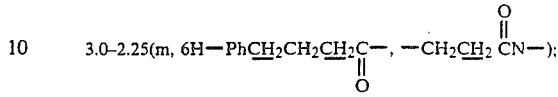
$^1$HNMR(CDCl$_3$): δ7.05(S, 5H, aromatic)3.65(t, 2H, CH$_2$NC—);

3.0-2.25(m, 6H—PhC$\underline{H}_2$CH$_2$C$\underline{H}_2$C—, —CH$_2$C$\underline{H}_2$ CN—);

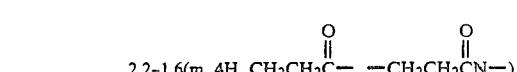
2.2-1.6(m, 4H, CH$_2$C$\underline{H}_2$C—, —C$\underline{H}_2$CH$_2$CN—)

HPLC: μ Bondapak-C18, ⌀=3.9 mm, size: 10μ
eluant: KH$_2$PO$_4$ 0.05M/CH$_3$CN (55:45)
Flow rate: 1 ml/min
Retention Time=10.56 min.

EXAMPLE 5

Preparation of 1-(nicotinoyl)-2-pyrrolidinone (ST 621)

1-nicotinoyl-2-pyrrolidinone was prepared as described in J. Org. Chem. 37, 1635, 1972.
M.P.: 98°–100° C.
TLC: silica gel; eluant ethyl acetate:hexane 8:2
RF=0.37
Elementary analysis: ($C_{10}H_{10}N_2O_2$); Calculated (%): C, 63.15; H, 5.3; N, 14.7. Found (%): C, 62.96; H, 5.24; N, 14.01.

$^1$H NMR (CDCl$_3$): δ8.8–8.6 (m, 2H, aromatic); 7.95–7.7 (m, 1H, aromatic), 7.45–7.15 (m, 1H, aromatic), 3.95

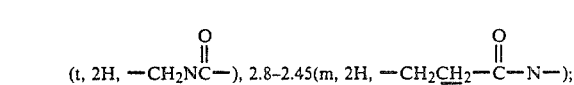
(t, 2H, —CH$_2$NC—), 2.8-2.45(m, 2H, —CH$_2$C$\underline{H}_2$—C—N—);

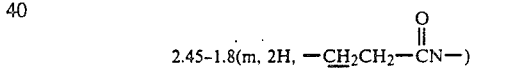
2.45-1.8(m, 2H, —C$\underline{H}_2$CH$_2$—CN—)

HPLC: μ Bondapack-C18, L=300 mm, ⌀=3.9, size=10μ
Mobile phase: KH$_2$PO$_4$ 0.5M/CH$_3$CN (80:20)
Flow rate: 1 ml/min
Retention Time=5.17 min

EXAMPLE 6

Preparation of 1-(carbobenzoxy-L-prolyl)-2-pyrrolidione (ST 686)

The product was prepared as in example 1.
The acid chloride, pyrrolidinone and triethylamine were reacted at 1:3:1 ratio.
Chromatography on silica gel was conducted with ethyl acetate-hexane (ratio 8:2) as eluant. The resulting oil was taken up with ethyl ether and yielded a white solid by crystallisation.
Yield: 30%
M.P.: 76°–77° C.
$[\alpha]_D^{20} = -62.6°$ MeOH (C=5)
TLC: silica gel; eluant ethyl acetate:hexane 8:2.
RF: 0.6
Elementary analysis: ($C_{17}H_{20}N_2O_4$); Calculated (%): C, 64.54; H, 6.37; N, 8.85. Found (%): C, 64.40; H, 6.35; N, 8.65.

$^1$H NMR (CDCl$_3$): 7.45–7.2 (m, 5H, aromatic), 5.45–5.35 (m, 1H, —CH$_2$CHN—), 5.25–4.95 (m, 2H, PhCH$_2$O—), 4.0–3.4

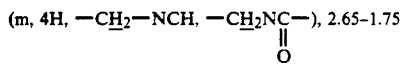
(m, 4H, —CH$_2$—NCH, —CH$_2$NC—), 2.65–1.75
∥
O

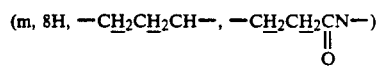
(m, 8H, —CH$_2$CH$_2$CH—, —CH$_2$CH$_2$CN—)
∥
O

HPLC Techopak-C$_{18}$, ∅=4 mm, L=300 mm, size=10μ
eluant KH$_2$PO$_4$ 0.05M-CH$_3$CN (60/40)
Flow rate: 1 ml/min
Retention Time=9.75 min The activity of the compounds of the invention was assessed in several pharmacological tests. Some of these tests wherein aniracetam was used as reference standard are illustrated hereinbelow.

(A) Assessment of Learning and Memory.

In order to assess learning and memory the passive avoidance test in mice was used (cfr. Bammer, Pharmacological investigations of neurotransmitter involvement in passive avoidance responding: a Review and some new results. Neurosci. Biobehav. Rev., 6 (3) 247–296, 1982); amnesia was brought about by electroconvulsive shock (ECS) (cfr. Banfi et al., A screening method for substances potentially active on learning and memory. J. Pharmacol. Methods Vol: 8 (4) 255–263, 1982 and Butler et al., Amnesia-reversal activity of a series of N[(disusbstituted-amino)alkyl]-2-oxo-1-pyrrolidineacetamides, including Pramiracetam. J. Med. Chem., 27, N. 5, 684–691, 1984). Male albino CD1 mice (Charles River—Germany) fed on a normal diet, were used. The compounds were administered i.p.; doses equimolar to 140,14 and 1.4 mg aniracetam kg$^{-1}$ were used.

The water-soluble compounds were dissolved in saline; the insoluble ones were dissolved indimethylsulfoxide and then diluted in 2% Tween 80, ratio 1:4.

The apparatus for passive avoidance conditioning was a black plastic chamber (42×42 cm, height 40 cm) provided with a floor constructed of metal rods that could be electrified. From the front wall extended a white runway, 30 cm long and 10 cm wide provided with side walls 12 cm high, which led into the box through a guillotine door. The runway was lightened by a 60 W lamp (cfr. Ader et al., Retention of passive avoidance response as a function of the intensity and duration of electric shock. Psychon. Sci., 26 (3), 125–127, 1972).

The animals, 30 minutes following treatment, were placed on the runway. After one minute of adaptation, the door was raised and the time employed by the animal to enter the darkened box with all four feet, was recorded.

Upon entry, the guillotine door was lowered and 5 seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec, duration 0.5 s, frequency 50 Hz). Retention was assessed 24 hours later by placing the animal on the runway and again evaluating the latency in entering the chamber, using an endpoint of 300 s (cfr. Bammer, loc. cit.).

The results of each compound under examination were expressed as percentage of amnesia reversal in order to make comparisons across the tested compounds.

As described in Butler et al. (loc. cit.), two groups of control animals were used on each experiment: (1) a ceiling control group (no ECS plus placebo injection), to ensure that the training was successful and that untreated animals remembered the task; and (2) a base-line control group (ECS plus placebo), to ensure that ECS produced amnesia for the task in untreated animals.

Typically, in this retention test 70–100% of the animals of the ceiling control group would remember the response and exhibit a latency to enter the darkened chamber higher than 250 s.

Consequently, an animal was regarded as being under amnesia whenever its latency to enter the darkened chamber during the retention test was less than 50% of the average time of the animals of the ceiling control group.

To assess amnesia reversal AR), the equation employed was as follows: % amnesia reversal =

$$= \frac{\text{(drug group)} - \text{(base-line control group)}}{\text{(ceiling control group)} - \text{(base-line control group)}} \times 100$$

If the base-line control group had more than 30% of the animals remembering the task, the data for the entire day was discarded. If there was not a separation between base-line and ceiling control groups of at least 40% correct retention, the data for the entire experiment was similarly discarded.

At the dose of 1.4 mg/kg, amnesia reversal of ST 628 and 686 were 36% and 47% respectively, whereas aniracetam AR was 30%.

(B) Behavioural Profile.

The behavioural profile was assessed in Swiss albino male mice weighing 22–24 g, using the Irwin test (IRWIN S., Drug screening and evaluative procedures. 136, 123–128, 1962). The animals had been caged under normal conditions and kept fasting for the last 18 hours. Following administration of the compounds, the behaviour of the animals was monitored for 6 hours. The parameters taken into account fell into three categories: the first one, strictly behavioural; the second one, neurological and the third one, relating to the autonomous nervous system.

Response by the animals were given an arbitrary score which took into account the characteristics exhibited by the control animals. The compound ST 621 was dissolved in water, whereas aniracetam and the compounds ST 623, 628, 643, 678 and 686 were suspended in 10% arabic gum.

The compounds were administered orally, via a gastric probe, at doses equimolar to 140; 35; 9 and 2 mg aniracetam/10 ml/kg.

All the compounds gave negative results in the Irwin test. Moreover, the compounds did not show any analgesic activity.

The compounds of the present invention can be formulated into orally or parenterally administrable pharmaceutical compositions. Suitable excipients and compositions for tablets, vials and the like are illustrated in the afore-said Canadian patent 1,100,515.

Pharmaceutical compositions in unit dosage form comprise between about 100 and about 500 mg of active ingredient.

What is claimed is:

1. 1-Acyl-2-pyrrolidinone of the formula (I)

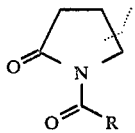

wherein R is
N-carbobenzoxy pyrrolidin-2-yl.

2. A method for enhancing learning and memory comprising orally or parenterally administering a learning-and-memory-enhancing effective amount of a 1-acyl-2-pyrrolidinone of the formula (I)

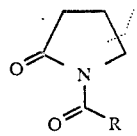

wherein R is selected from the group consisting of:
  phenyl substituted with halogen-substituted $C_1$–$C_4$ alkyl;
  phenylalkyl wherein the alkyl moiety has 3 or 4 carbon atoms;
  phenylethenyl wherein the phenyl moiety is substituted with halogen-substituted $C_1$–$C_4$ alkyl;
  N-carbobenzoxy pyrrolidin-2-yl; and
  pyrid-3-yl;
to a patient in need of such treatment.

* * * * *